(12) United States Patent
Ferguson

(10) Patent No.: US 6,428,564 B1
(45) Date of Patent: Aug. 6, 2002

(54) MEDICAL CONDITION SEAT CUSHION SYSTEM

(76) Inventor: Patricia A. Ferguson, 7235 Ten Hill Rd., W. Bloomfield, MI (US) 48322

( * ) Notice: Subject to any disclaimer, the term of this patent is extended or adjusted under 35 U.S.C. 154(b) by 0 days.

(21) Appl. No.: 09/451,330

(22) Filed: Nov. 30, 1999

(51) Int. Cl.[7] .................................................. A61F 7/00
(52) U.S. Cl. .......................... 607/114; 607/108; 5/653; 5/421; 602/67
(58) Field of Search ................................ 607/108, 114, 607/112; 602/67, 14; 601/15; 5/653, 421

(56) References Cited

U.S. PATENT DOCUMENTS

| | | | | |
|---|---|---|---|---|
| 2,249,298 A | * | 7/1941 | Ratti | 128/24 |
| 3,175,558 A | * | 3/1965 | Caillouette et al. | 128/403 |
| 4,240,436 A | * | 12/1980 | Singleton | 128/403 |
| 4,932,089 A | * | 6/1990 | Laviero | 5/421 |
| 5,916,088 A | * | 6/1999 | Gueli | 5/639 |
| 6,010,528 A | * | 1/2000 | Augustine et al. | 607/104 |
| 6,042,604 A | * | 3/2000 | Gennetti | 607/108 |

* cited by examiner

*Primary Examiner*—Linda C. M. Dvorak
*Assistant Examiner*—Jocelyn Ram
(74) *Attorney, Agent, or Firm*—Joseph N. Breaux

(57) ABSTRACT

A system for the easing of medical conditions such as episiotomy sites and hemorrhoids by applying a temperature transferring element against the site to either apply cooling or heating to the affected area. The medical condition seat cushion system provides a cushion having a cavity within which a medical compress having a temperature transferring element is suspended. In addition, the medical compress includes an absorbent cover which may be saturated with witch hazel, lidocaine, or other disinfectant or pain relieving mixture.

8 Claims, 4 Drawing Sheets

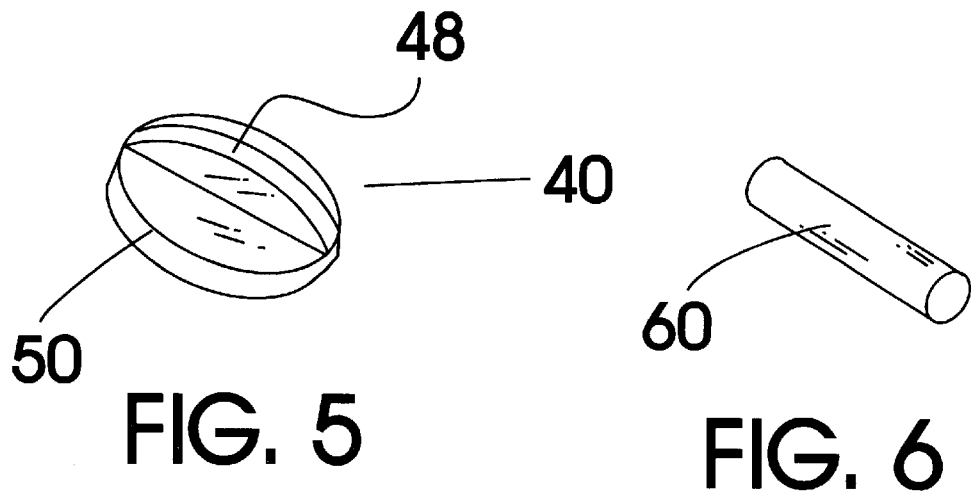
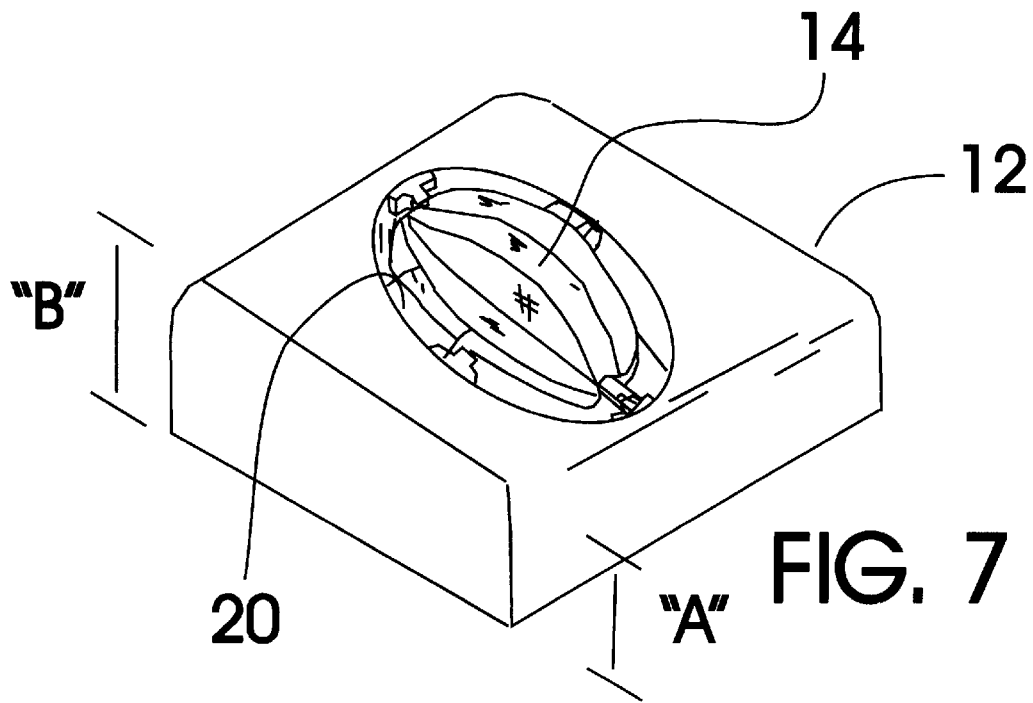

MEDICAL CONDITION SEAT CUSHION SYSTEM

TECHNICAL FIELD

The present invention relates to medical treatment systems and more particularly to a medical condition seat cushion system that includes a cushion assembly and a medical compress assembly; the cushion assembly being formed from a compressible foam and having a cavity formed into a top surface having a number of fastening elements positioned around an edge defining a top opening into the cavity; the medical compress assembly including temperature transferring element positioned within an absorbent cover provided with companionate fastener tabs for securing the medical compress assembly above the cavity; the medical compress assembly being positioned to contact a medical treatment site of a patient seated on the cushion assembly when the medical compress assembly is positioned above the cavity.

BACKGROUND ART

The easing of medical conditions such as episiotomy sites and hemorrhoids can often be accomplished by applying a temperature transferring element against the site to either apply cooling or heating to the affected area. It would be desirable, therefore, to have a medical condition seat cushion system that provided a cushion having a cavity within which a medical compress assembly having a temperature transferring element is suspended which would provide a convenient means for holding the medical compress against the desired treatment area. In addition, because these sites can be painful, it would be a further benefit if the medical compress assembly included an absorbent cover which could be saturated with witch hazel, lidocaine, or other disinfectant or pain relieving mixture. Because exudates are often associated with these types of conditions, it would be desirable if the cushion had a cavity that was lined by a fluid impermeable surface or if a number of disposable fluid impermeable liners were provided for placement within the cavity during use.

GENERAL SUMMARY DISCUSSION OF INVENTION

It is thus an object of the invention to provide a medical condition seat cushion system that includes a cushion assembly and a medical compress assembly; the cushion assembly being formed from a compressible foam and having a cavity formed into a top surface having a number of fastening elements positioned around an edge defining a top opening into the cavity; the medical compress assembly including temperature transferring element positioned within an absorbent cover provided with companionate fastener tabs for securing the medical compress assembly above the cavity; the medical compress assembly being positioned to contact a medical treatment site of a patient seated on the cushion assembly when the medical compress assembly is positioned above the cavity.

It is a further object of the invention to provide a medical condition seat cushion system as described above wherein the temperature transferring element transfers heat to a patient.

It is a still further object of the invention to provide a medical condition seat cushion system as described above wherein the temperature transferring element transfers cold to a patient.

It is a still further object of the invention to provide a medical condition seat cushion system as described above wherein the cavity is lined by a fluid impermeable surface.

It is a still further object of the invention to provide a medical condition seat cushion system as described above wherein a number of disposable fluid impermeable liners are included and sized and shaped to be positioned within the cavity during use.

It is a still further object of the invention to provide a medical condition seat cushion system that accomplishes all or some of the above objects in combination.

Accordingly, a medical condition seat cushion system is provided. The medical condition seat cushion system includes a cushion assembly and a medical compress assembly; the cushion assembly being formed from a compressible foam and having a cavity formed into a top surface having a number of fastening elements positioned around an edge defining a top opening into the cavity; the medical compress assembly including temperature transferring element positioned within an absorbent cover provided with companionate fastener tabs for securing the medical compress assembly above the cavity; the medical compress assembly being positioned to contact a medical treatment site of a patient seated on the cushion assembly when the medical compress assembly is positioned above the cavity. The term "temperature transferring element" is used herein to mean either a heating or a cooling device.

In one preferred embodiment, the medical compress is an episiotomy medical compress assembly that includes a shaped freezable member filled with a freezable mixture that is positioned within an absorbent cover provided with companionate fastener tabs for securing the episiotomy medical compress assembly above the cavity, the shaped freezable member having a curved shaped portion rising upward from a base portion so as to contact the site of an episiotomy between the vagina and the anus of a patient when a patient is seated on the cushion and the episiotomy medical compress assembly is positioned above the cavity with the curved shaped portion directed upward away from an interior of the cavity.

In another preferred embodiment, the medical compress assembly is a hemorrhoid medical compress assembly including a rod shaped heat generating insert positioned within an absorbent cover provided with companionate fastener tabs for securing the hemorrhoid medical compress assembly above the cavity, the rod shaped heat generating insert being sized to fit between the buttocks of a user and contact the hemorrhoids extending from the anus when a patient is seated on the cushion and the hemorrhoid medical compress assembly is positioned and secured above the cavity.

In still another preferred embodiment, the cavity is defined by a fluid impermeable surface.

In a still another preferred embodiment, the medical condition seat cushion system further includes a number of disposable fluid impermeable liners that are sized and shaped to be positioned within the cavity during use.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 5 is a perspective view of the shaped freezable member filled with a freezable mixture of the episiotomy medical compress assembly in isolation showing the curved shaped portion rising upward from the base portion.

FIG. 6 is a perspective view of the rod shaped chemical heat generating insert of the hemorrhoid medical compress assembly in isolation.

FIG. 7 is a perspective view of the episiotomy medical compress assembly positioned above the cavity of the cushion assembly with the curved shaped portion directed upward away from an interior of the cavity.

EXEMPLARY MODE FOR CARRYING OUT THE INVENTION

Figure 2:
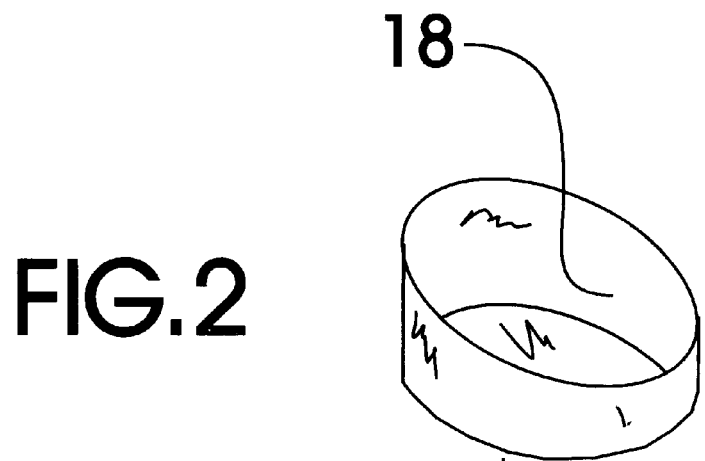
FIG. 2 is a perspective view of an exemplary liner member.
Figure 1:
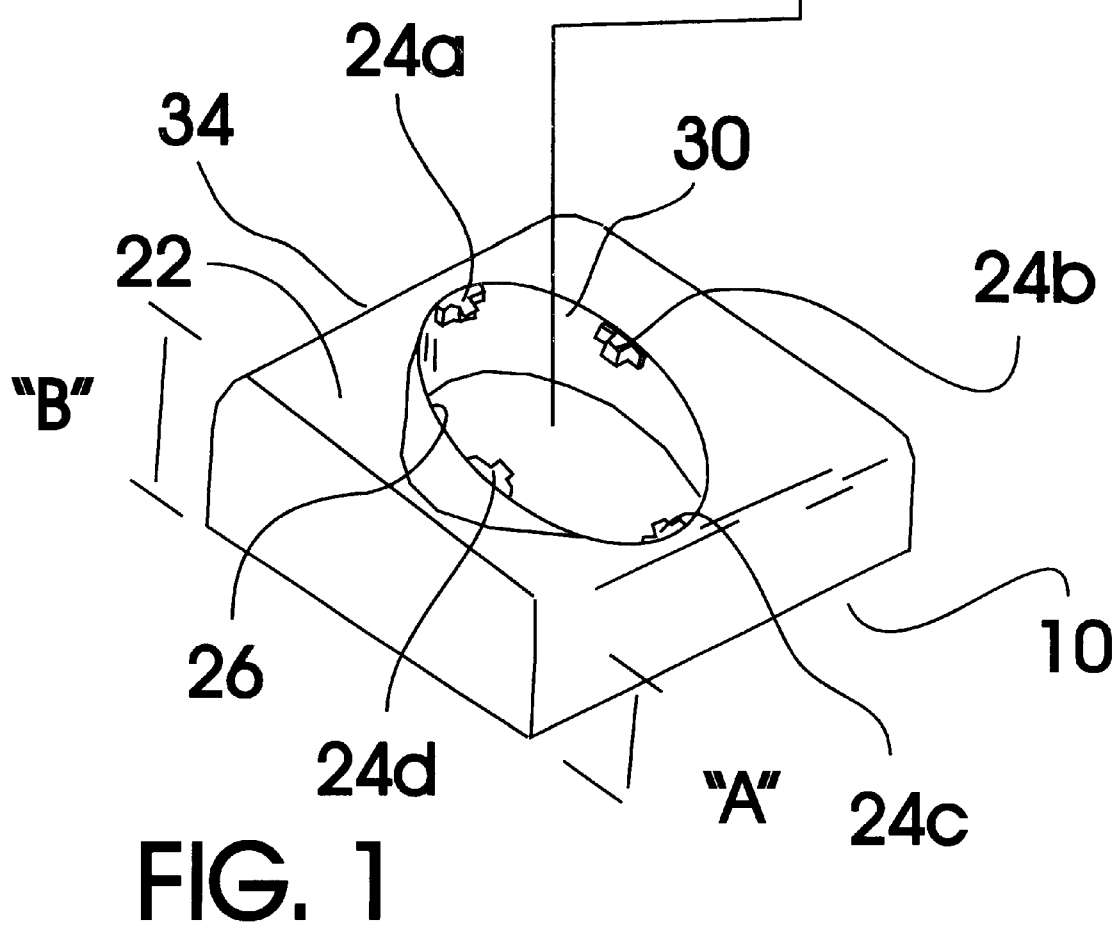
FIG. 1 is a perspective view of an exemplary cushion assembly.
Figure 4:
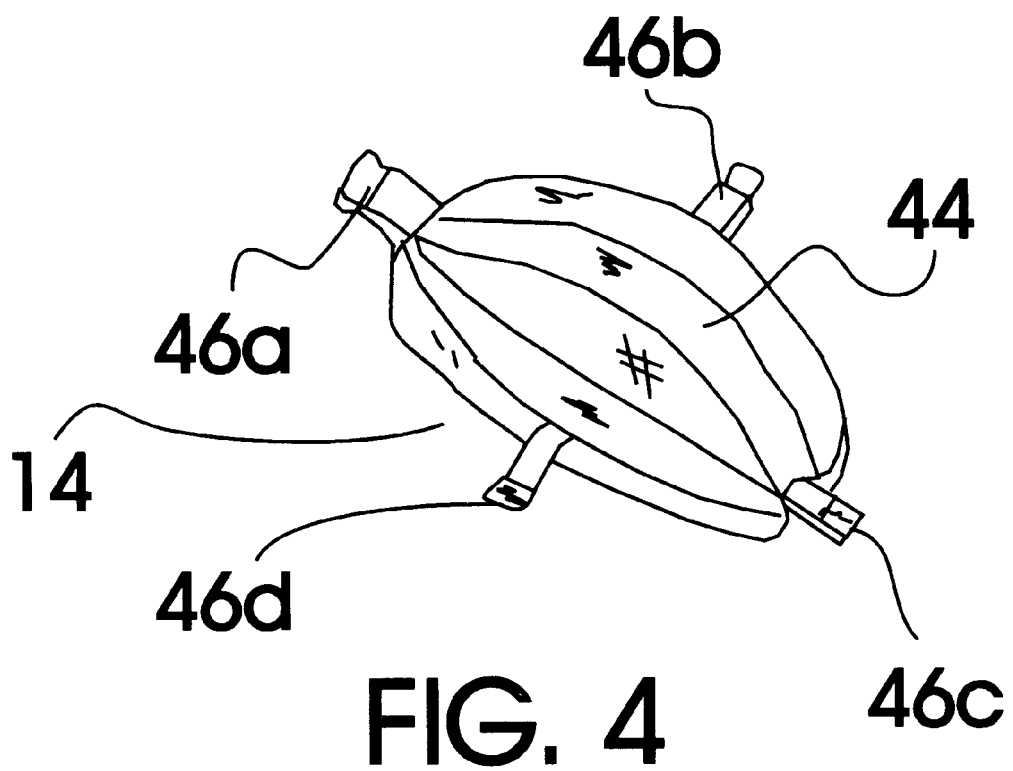
FIG. 4 is a perspective view of an exemplary episiotomy medical compress assembly.
Figure 3:
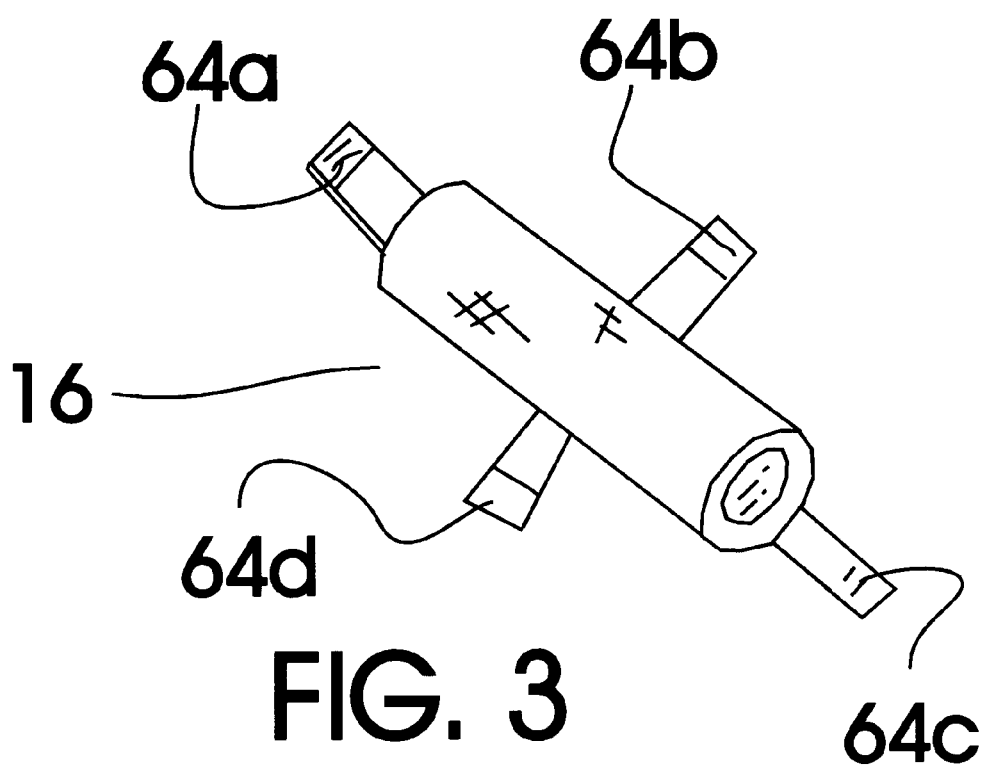
FIG. 3 is a perspective view of an exemplary hemorrhoid medical compress assembly.
Figure 8:
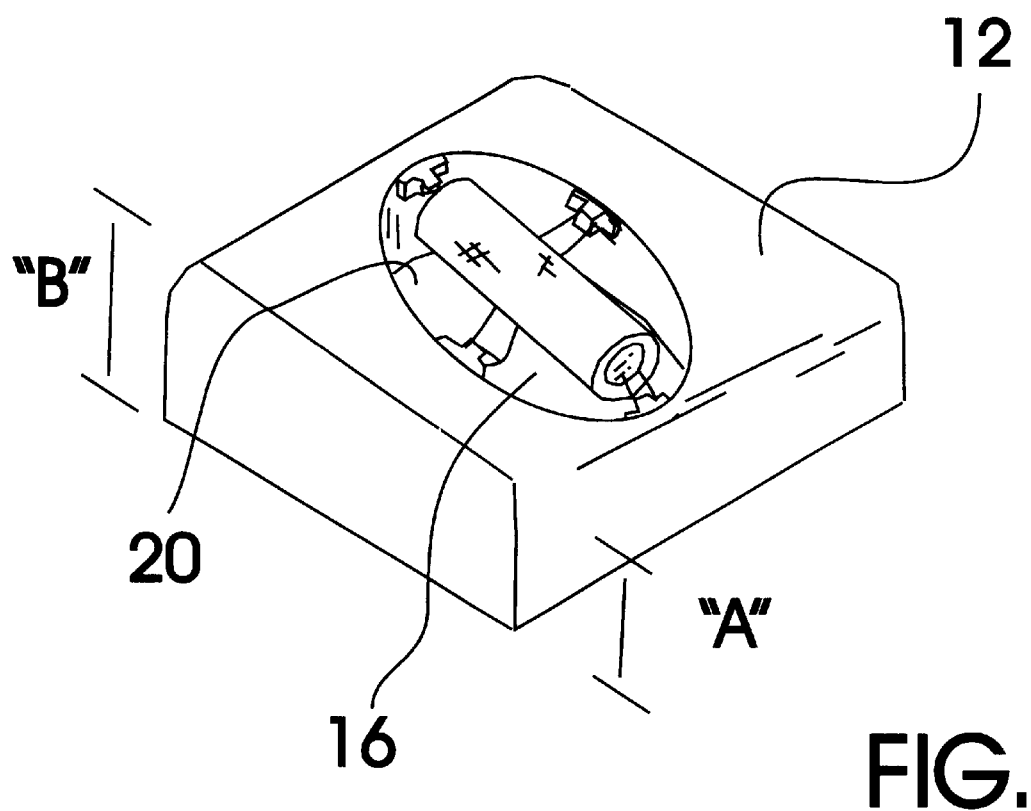
FIG. 8 is a perspective view of the hemorrhoid medical compress assembly positioned above the cavity of the cushion assembly situated to fit between the buttocks of a user sitting on the cushion assembly.

FIG. 1–8 shows an exemplary embodiment of the medical condition seat cushion system of the present invention, generally designated 10. Medical condition seat cushion system 10 includes a cushion assembly, generally designated 12; an episiotomy medical compress assembly, generally designated 14; a hemorrhoid medical compress assembly, generally designated 16; and a number of identical disposable liner members 18 (only one shown).

Cushion assembly 12 is formed from a compressible foam and has a cavity 20 formed into a top surface 22 thereof. Four hook and pile fastening elements 24a–d are secured and positioned around an edge 26 defining a top opening into cavity 20. In this embodiment, cavity 20 is defined by a fluid impermeable surface 30 and a front end 33 of cushion 12 has a thickness "A" that is greater than the thickness "B" of back end 34 of cushion 12. Front end 33 and back end 34 can of course be equal thickness if desired. The disposable liner members 18 are formed from a fluid impermeable plastic and are sized and shaped to be positionable within cavity 20 during use.

Episiotomy medical compress assembly 14 includes a plastic, freezable gel filled, shaped freezable member, generally designated 40, that is positioned within an absorbent cover 44 that is provided with four companionate fastener tabs 46a–d for securing episiotomy medical compress assembly 14 above cavity 20 of cushion 12 using hook and pile fastening elements 24a–d during use. Shaped freezable member 40 has a curved shaped portion 48 rising upward from a base portion 50 so as to contact the site of an episiotomy between the vagina and the anus of a patient when a patient is seated on cushion 12 and episiotomy medical compress assembly 14 is positioned above the cavity 20 with curved shaped portion 48 directed upward away from cavity 20.

Hemorrhoid medical compress assembly 16 includes a chemical, rod shaped heat generating insert 60 that is positionable within an absorbent cover 62 provided with four companionate fastener tabs 64a–d for securing hemorrhoid medical compress assembly 16 above cavity 20 with hook and pile fastening elements 24a–d during use. Rod shaped heat generating insert 60 is sized to fit between the buttocks of a user and contact the hemorrhoids extending from the anus when a patient is seated on cushion 12 and hemorrhoid medical compress assembly 16 is positioned and secured above cavity 20.

It can be seen from the preceding description that a medical condition seat cushion system has been provided.

It is noted that the embodiment of the medical condition seat cushion system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A medical condition seat cushion system comprising:

a cushion assembly; and a medical compress assembly;

said cushion assembly being formed from a compressible foam and having a cavity formed into a top surface having a number of fastening elements positioned around an edge defining a top opening into said cavity;

said medical compress assembly including a temperature transferring element positioned within an absorbent cover provided with companionate fastener tabs for securing said medical compress assembly above said cavity;

said medical compress assembly being adapted to be positioned to contact a medical treatment site of a patient seated on said cushion assembly while said medical compress assembly remains positioned above said cavity;

said cavity being defined by a fluid impermeable surface.

2. The medical condition seat cushion system of claim 1 wherein:

said medical compress assembly is an episiotomy medical compress assembly that includes a shaped freezable member filled with a freezable mixture that is positioned within an absorbent cover provided with companionate fastener tabs for securing said episiotomy medical compress assembly above said cavity, said shaped freezable member having a curved shaped portion rising upward from a base portion so as to contact a site of an episiotomy between a vagina and an anus of a patient when a patient is seated on said cushion and said episiotomy medical compress assembly is positioned above said cavity with said curved shaped portion directed upward away from an interior of said cavity.

3. The medical condition seat cushion system of claim 1 wherein:

said medical compress assembly is a hemorrhoid medical compress assembly including a rod shaped heat generating insert positioned within an absorbent cover provided with companionate fastener tabs for securing said hemorrhoid medical compress assembly above said cavity, said rod shaped heat generating insert being sized to fit between two buttocks of a user and contact hemorrhoids extending from an anus when a patient is seated on said cushion and said hemorrhoid medical compress assembly is positioned and secured above said cavity.

4. A medical condition seat cushion system comprising:

a cushion assembly; and a medical compress assembly;

said cushion assembly being formed from a compressible foam and having a cavity formed into a top surface having a number of fastening elements positioned around an edge defining a top opening into said cavity;

said medical compress assembly including a temperature transferring element positioned within an absorbent cover provided with companionate fastener tabs for securing said medical compress assembly above said cavity;

said medical compress assembly being adapted to be positioned to contact a medical treatment site of a patient seated on said cushion assembly while said medical compress assembly remains positioned above said cavity;

said medical compress assembly being an episiotomy medical compress assembly that includes a shaped freezable member filled with a freezable mixture that is positioned within an absorbent cover provided with companionate fastener tabs for securing said episiotomy medical compress assembly above said cavity, said shaped freezable member having a curved shaped portion rising upward from a base portion so as to contact a site of an episiotomy between a vagina and an anus of a patient when a patient is seated on said cushion and said episiotomy medical compress assembly is positioned above said cavity with said curved shaped portion directed upward away from an interior of said cavity.

5. A medical condition seat cushion system comprising:

a cushion assembly; and a medical compress assembly;

said cushion assembly being formed from a compressible foam and having a cavity formed into a top surface having a number of fastening elements positioned around an edge defining a top opening into said cavity;

said medical compress assembly including a temperature transferring element positioned within an absorbent cover provided with companionate fastener tabs for securing said medical compress assembly above said cavity;

said medical compress assembly being adapted to be positioned to contact a medical treatment site of a patient seated on said cushion assembly while said medical compress assembly remains positioned above said cavity;

said medical compress assembly is a hemorrhoid medical compress assembly including a rod shaped heat generating insert positioned within an absorbent cover provided with companionate fastener tabs for securing said hemorrhoid medical compress assembly above said cavity, said rod shaped heat generating insert being sized to fit between two buttocks of a user and contact hemorrhoids extending from the anus when a patient is seated on said cushion and said hemorrhoid medical compress assembly is positioned and secured above said cavity.

6. A medical condition seat cushion system comprising:

a cushion assembly; and a medical compress assembly;

said cushion assembly being formed from a compressible foam and having a cavity formed into a top surface having a number of fastening elements positioned around an edge defining a top opening into said cavity;

said medical compress assembly including a temperature transferring element positioned within an absorbent cover provided with companionate fastener tabs for securing said medical compress assembly above said cavity;

said medical compress assembly being adapted to be positioned to contact a medical treatment site of a patient seated on said cushion assembly while said medical compress assembly remains positioned above said cavity;

a number of disposable fluid impermeable liners that are sized and shaped to be positioned within said cavity during use.

7. The medical condition seat cushion system of claim 6 wherein:

said medical compress assembly is an episiotomy medical compress assembly that includes a shaped freezable member filled with a freezable mixture that is positioned within an absorbent cover provided with companionate fastener tabs for securing said episiotomy medical compress assembly above said cavity, said shaped freezable member having a curved shaped portion rising upward from a base portion so as to contact a site of an episiotomy between a vagina and an anus of a patient when a patient is seated on said cushion and said episiotomy medical compress assembly is positioned above said cavity with said curved shaped portion directed upward away from an interior of said cavity.

8. The medical condition seat cushion system of claim 6 wherein:

said medical compress assembly is a hemorrhoid medical compress assembly including a rod shaped heat generating insert positioned within an absorbent cover provided with companionate fastener tabs for securing said hemorrhoid medical compress assembly above said cavity, said rod shaped heat generating insert being sized to fit between two buttocks of a user and contact hemorrhoids extending from an anus when a patient is seated on said cushion and said hemorrhoid medical compress assembly is positioned and secured above said cavity.

* * * * *